United States Patent
Frakes et al.

(10) Patent No.: US 10,643,360 B2
(45) Date of Patent: May 5, 2020

(54) REAL-TIME MEDICAL IMAGE VISUALIZATION SYSTEMS AND RELATED METHODS

(71) Applicant: ARIZONA BOARD OF REGENTS ON BEHALF OF ARIZONA STATE UNIVERSITY, Scottsdale, AZ (US)

(72) Inventors: David Frakes, Scottsdale, AZ (US); Ross Maciejewski, Phoenix, AZ (US); Mark Spano, Casa Grande, AZ (US); Dustin Plaas, Gilbert, AZ (US); Alison Van Putten, Phoenix, AZ (US); Joseph Sansone, Phoenix, AZ (US); Matthew Mortensen, Chandler, AZ (US); Nathaniel Kirkpatrick, Atlanta, GA (US); Jonah Thomas, Chandler, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 1 day.

(21) Appl. No.: 15/893,404

(22) Filed: Feb. 9, 2018

(65) Prior Publication Data
US 2018/0232925 A1    Aug. 16, 2018

Related U.S. Application Data

(60) Provisional application No. 62/457,545, filed on Feb. 10, 2017.

(51) Int. Cl.
*G06K 9/00* (2006.01)
*G06T 11/60* (2006.01)
(Continued)

(52) U.S. Cl.
CPC .............. *G06T 11/60* (2013.01); *A61B 90/36* (2016.02); *A61B 2034/2065* (2016.02);
(Continued)

(58) Field of Classification Search
USPC ................................... 382/115–127, 128–134
See application file for complete search history.

(56) References Cited

U.S. PATENT DOCUMENTS 7,171,255 B2    1/2007  Holupka et al.
7,356,367 B2    4/2008  Liang et al.
(Continued)

FOREIGN PATENT DOCUMENTS

| WO | 2014152919 A1 | 9/2014 |
| WO | 2014152929 A1 | 9/2014 |
| WO | 2015112993 A1 | 7/2015 |

*Primary Examiner* — Alex Kok S Liew
(74) *Attorney, Agent, or Firm* — Norton Rose Fulbright US LLP

(57) ABSTRACT

Some systems include a memory, and a processor coupled to the memory, wherein the processor is configured to: identify one or more spatial markers in a medical data-based image of a patient, identify one or more spatial markers in a real-time perceived image of the patient, wherein the one or more spatial markers in the medical data-based image correspond to an anatomical feature of the patient and the one or more spatial markers in the real-time perceived image correspond to the anatomical feature of the patient, superimpose the medical data-based image of the patient with the real-time perceived image of the patient, and align the one or more spatial markers in the medical data-based image with the respective one or more spatial markers in the real-time perceived image.

19 Claims, 3 Drawing Sheets

(51) Int. Cl.
*A61B 90/00* (2016.01)
*A61B 34/20* (2016.01)
*A61B 90/50* (2016.01)

(52) U.S. Cl.
CPC ... *A61B 2090/365* (2016.02); *A61B 2090/372* (2016.02); *A61B 2090/502* (2016.02); *G06T 2200/24* (2013.01); *G06T 2210/41* (2013.01)

(56) References Cited

U.S. PATENT DOCUMENTS

| | | | |
|---|---|---|---|
| 8,259,161 B1* | 9/2012 | Huang | G03B 35/02 |
| | | | 348/50 |
| 8,730,268 B2 | 5/2014 | Zwart et al. | |
| 9,710,916 B2 | 7/2017 | Thiagarajan et al. | |
| 9,779,497 B2 | 10/2017 | Thiagarajan et al. | |
| 10,290,230 B2 | 5/2019 | Babiker et al. | |
| 2003/0190060 A1* | 10/2003 | Pengwu | G06K 9/00268 |
| | | | 382/118 |
| 2004/0005088 A1* | 1/2004 | Jeung | A61B 5/08 |
| | | | 382/128 |
| 2005/0031176 A1* | 2/2005 | Hertel | G06T 7/33 |
| | | | 382/128 |
| 2008/0085042 A1* | 4/2008 | Trofimov | A61B 5/042 |
| | | | 382/128 |
| 2009/0262992 A1* | 10/2009 | Markowitz | A61B 5/06 |
| | | | 382/128 |
| 2015/0238271 A1* | 8/2015 | Wollowick | A61B 6/12 |
| | | | 600/436 |
| 2017/0098019 A1 | 4/2017 | Yadollahi-Farsani et al. | |
| 2018/0092690 A1 | 4/2018 | Nair et al. | |

* cited by examiner

REAL-TIME MEDICAL IMAGE VISUALIZATION SYSTEMS AND RELATED METHODS

PRIORITY

This application claims the benefit of U.S. Provisional Application No. 62/457,545, filed Feb. 10, 2017. The entire contents of the referenced application are incorporated into the present application by reference.

BACKGROUND

2. Technical Field

The present invention relates generally to medical image visualization, and more specifically, but not by way of limitation, to real-time medical image visualization systems and related methods.

2. Description of Related Art

Examples of systems and methods for medical image visualization are disclosed in U.S. Pat. Nos. 7,171,255, and 7,356,367.

SUMMARY

Some embodiments of the present systems and methods are configured to align and/or superimpose (e.g., graphical) medical data with a perceived image of a patient (e.g., in real time). As such, the present systems and methods may provide instructional and/or diagnostic relevance. The present systems and methods may provide health professionals a better spatial understanding (e.g., prior to and/or after a medical procedure, such as, for example, a surgery), thereby reducing a risk of extended medical procedure time, reducing a risk of committing mistakes during the medical procedure, and/or the like. For example, the present systems and methods may depict hemodynamics in a patient's body, which may allow (e.g., a real-time) evaluation and diagnostics (e.g., after the conclusion of a medical procedure) and thereby provide a better understanding of the current blood flow in various locations in the patient's body. For further example, the present systems and methods may demonstrate to healthcare personnel the orientation, location, and/or spatial relevance of anatomical structures without the need to open tissue.

Some embodiments of the present systems comprise a memory; and a processor coupled to the memory; wherein the processor is configured to: identify one or more spatial markers in a medical data-based image of a patient; identify one or more spatial markers in a real-time perceived image of the patient, wherein the one or more spatial markers in the medical data-based image correspond to an anatomical feature of the patient and the one or more spatial markers in the real-time perceived image correspond to the anatomical feature of the patient; superimpose the medical data-based image of the patient with the real-time perceived image of the patient; and align the one or more spatial markers in the medical data-based image with the respective one or more spatial markers in the real-time perceived image.

Some embodiments of the present systems comprise one or more sensors configured to detect movement of the position of the one or more spatial markers in the real-time perceived image; and wherein the processor is configured to update the position of the one or more spatial markers of the medical data-based image in response to the detected movement of the position of the one or more spatial markers in the real-time perceived image. In some embodiments, the medical data-based image comprises at least one of the following: a computed axial tomography (CAT) image, a magnetic resonance imaging (MRI) image, a positron emission tomography (PET) image, an ultrasound image, and an x-ray image. In some embodiments, the anatomical feature of the patient comprises one or more of the following: one or both eye sockets, a mouth, one or both ears, and an anterior nasal aperture. In some embodiments, the real-time perceived image of the patient is captured by one or more sensors configured to capture an image.

Some embodiments of the present systems comprise a user interface device, wherein the user interface device is configured to include the memory and the processor. In some embodiments, the user interface device comprises a smartphone. In some embodiments, the user interface device comprises wearable computer glasses. In some embodiments, the user interface device comprises a tablet computer.

Some embodiments of the present computerized methods comprise: identifying one or more spatial markers in a medical data-based image of a patient; identifying one or more spatial markers in a real-time perceived image of the patient, wherein the one or more spatial markers in the medical data-based image correspond to an anatomical feature of the patient and the one or more spatial markers in the real-time perceived image correspond to the anatomical feature of the patient; simultaneously displaying the medical data-based image of the patient and the real-time perceived image of the patient; and align the one or more spatial markers in the medical data-based image with the one or more spatial markers in the real-time perceived image.

Some embodiments of the present systems comprise detecting movement of the one or more spatial markers in the real-time perceived image; and updating on a display a position of the one or more spatial markers of the medical data-based image in response to the detected movement of the one or more spatial markers in the real-time perceived image.

In some embodiments, the medical data-based image comprises at least one of the following: a computed axial tomography (CAT) image, a magnetic resonance imaging (MRI) image, a positron emission tomography (PET) image, an ultrasound image, and an x-ray image. In some embodiments, the anatomical feature of the patient comprises one or more of the following: one or both eye sockets, a mouth, one or both ears, and an anterior nasal aperture. In some embodiments, the real-time perceived image of the patient is captured by one or more sensors configured to capture an image.

The term "coupled" is defined as connected, although not necessarily directly, and not necessarily mechanically; two items that are "coupled" may be unitary with each other. The terms "a" and "an" are defined as one or more unless this disclosure explicitly requires otherwise. The term "substantially" is defined as largely but not necessarily wholly what is specified (and includes what is specified; e.g., substantially 90 degrees includes 90 degrees and substantially parallel includes parallel), as understood by a person of ordinary skill in the art. In any disclosed embodiment, the terms "substantially" and "approximately" may be substituted with "within [a percentage] of" what is specified, where the percentage includes 0.1, 1, 5, and 10 percent.

The phrase "and/or" means and or or. To illustrate, A, B, and/or C includes: A alone, B alone, C alone, a combination of A and B, a combination of A and C, a combination of B and C, or a combination of A, B, and C. In other words, "and/or" operates as an inclusive or.

Further, a device or system that is configured in a certain way is configured in at least that way, but it can also be configured in other ways than those specifically described.

The terms "comprise" (and any form of comprise, such as "comprises" and "comprising"), "have" (and any form of have, such as "has" and "having"), "include" (and any form of include, such as "includes" and "including"), and "contain" (and any form of contain, such as "contains" and "containing") are open-ended linking verbs. As a result, an apparatus that "comprises," "has," "includes," or "contains" one or more elements possesses those one or more elements, but is not limited to possessing only those elements. Likewise, a method that "comprises," "has," "includes," or "contains" one or more steps possesses those one or more steps, but is not limited to possessing only those steps.

Any embodiment of any of the apparatuses, systems, and methods can consist of or consist essentially of—rather than comprise/have/include/contain—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb.

The feature or features of one embodiment may be applied to other embodiments, even though not described or illustrated, unless expressly prohibited by this disclosure or the nature of the embodiments.

Some details associated with the embodiments are described above, and others are described below.

BRIEF DESCRIPTION OF THE DRAWINGS

The following drawings illustrate by way of example and not limitation. For the sake of brevity and clarity, every feature of a given structure is not always labeled in every figure in which that structure appears. Identical reference numbers do not necessarily indicate an identical structure. Rather, the same reference number may be used to indicate a similar feature or a feature with similar functionality, as may non-identical reference numbers.

DETAILED DESCRIPTION

Figure 1:
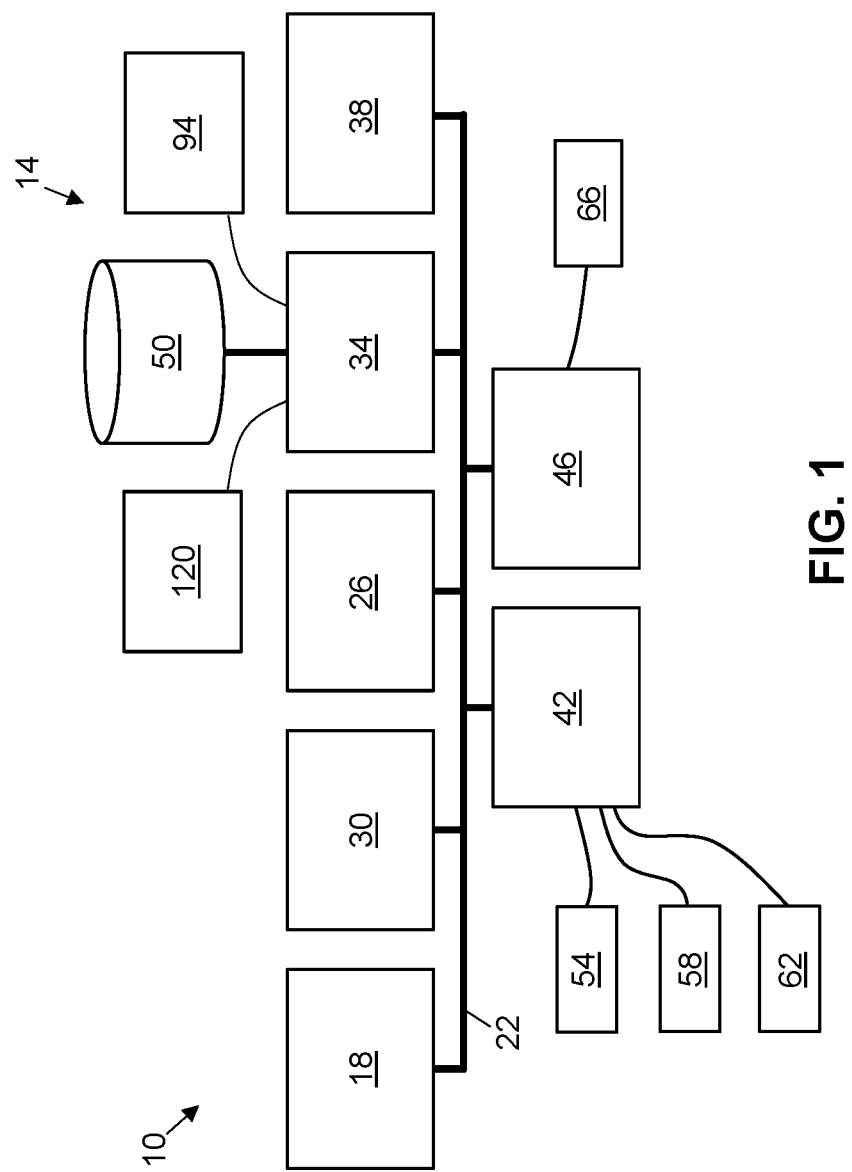
FIG. 1 is a schematic block diagram illustrating one of the present systems.

Referring now to the drawings, and more particularly to FIG. 1, shown therein is a representative hardware environment, which illustrates a typical hardware configuration of a computer system 10 that can be used to implement at least some of the present embodiments. The present embodiments are not limited to the architecture of system 10. Rather, system 10 is provided as an example of one type of computing system that may be adapted to perform the functions of a user interface device 14. User interface device 14 is referred to broadly and comprises a suitable processor-based device such as, for example, a mobile communication and/or organizer device (e.g., a cellular phone, smartphone, Personal Digital Assistant (PDA), and/or the like), wearable computer glasses (e.g., glasses with a transparent heads-up display (HUD), glasses with an augmented reality (AR) overlay, and/or the like), a tablet computer, a laptop computer, and/or the like. Persons of ordinary skill in the art may utilize any number of suitable user interface devices (e.g., 14) capable of executing logical operations according to the described embodiments.

The embodiments described in the present disclosure can be configured to be practiced in the context of an operating system resident on a user interface device (e.g., 14) having an Apple operating system (e.g., mobile operating system iOS and/or desktop operating system OS X), an Android mobile operating system, a Microsoft operating system (e.g., mobile operating system Windows Mobile and/or desktop operating system, such as, for example, Windows 7).

System 10 includes a central processing unit (CPU) 18 that is coupled to a system bus 22. CPU 18 may be a general purpose CPU or a microprocessor. The present embodiments are not restricted by the architecture of CPU 18, as long as the CPU supports the model(s), controller(s), view(s), configurations, and/or operations as described herein. CPU 18 may execute the various logical instructions according to the present embodiments. For example, CPU 18 may execute machine-level instructions according to the exemplary operations described below.

System 10 may include Random Access Memory (RAM) 26, which may be SRAM, DRAM, SDRAM, and/or the like. System 10 may utilize RAM 26 to store the various data structures used by a software application (e.g., 70) configured as described in this disclosure. System 10 may also include Read Only Memory (ROM) 30 which may be PROM, EPROM, EEPROM, optical storage, and/or the like. ROM 30 may store configuration information for booting computer system 10. RAM 26 and ROM 30 may also store user and/or system 10 data.

System 10 may also include an input/output (I/O) adapter 34, a communications adapter 38, a user interface adapter 42, and a display adapter 46. I/O adapter 34, communications adapter 38, and/or user interface adapter 42 may, in some embodiments, enable or a user to interact with system 10 (e.g., to input user credentials, to input patient medical data, to request patient medical data, to input patient information, such as, for example, to update a patient's medical record, respond to a prompt requesting information about characteristics of a patient, or the status of a medical procedure, and/or the like). In a further embodiment, display adapter 46 may display a graphical user interface associated with a software or web-based application (e.g., 70).

More particularly, I/O adapter 34 can be configured to connect one or more storage devices 50, such as one or more of a hard drive, a Compact Disk (CD) drive, a floppy disk drive, a tape drive, to system bus 22. I/O adapter 34 may also be configured to connect one or more sensors (e.g., 94, 120) to system bus 22. Communications adapter 38 may be adapted to couple system 10 to a network, which may, for example, be one or more of a LAN, WAN, and/or the Internet. User interface adapter 42 can be configured to connect user input devices, such as a touchscreen 54, a keyboard 58, a mouse 62, a speaker, a microphone, and/or the like to system bus 22. Display adapter 46 may be driven by CPU 18 to control a display 66 of user interface device 14.

In this embodiment, system 10 may host one or more software applications 70 (e.g., locally-, network-, and/or Internet-accessible software applications) configured and/or programmed to perform the functions described in this disclosure. For example, application 70 may include model(s), controller(s), and/or view(s), one or more of which are configured to interface with at least one component of system 10, a user (e.g., via user interface device 14), and/or the like. The framework architecture, which can be resident in the RAM 26 and under the control of the CPU 18, can be responsible for implementing the functions described in this disclosure.

Figure 2:
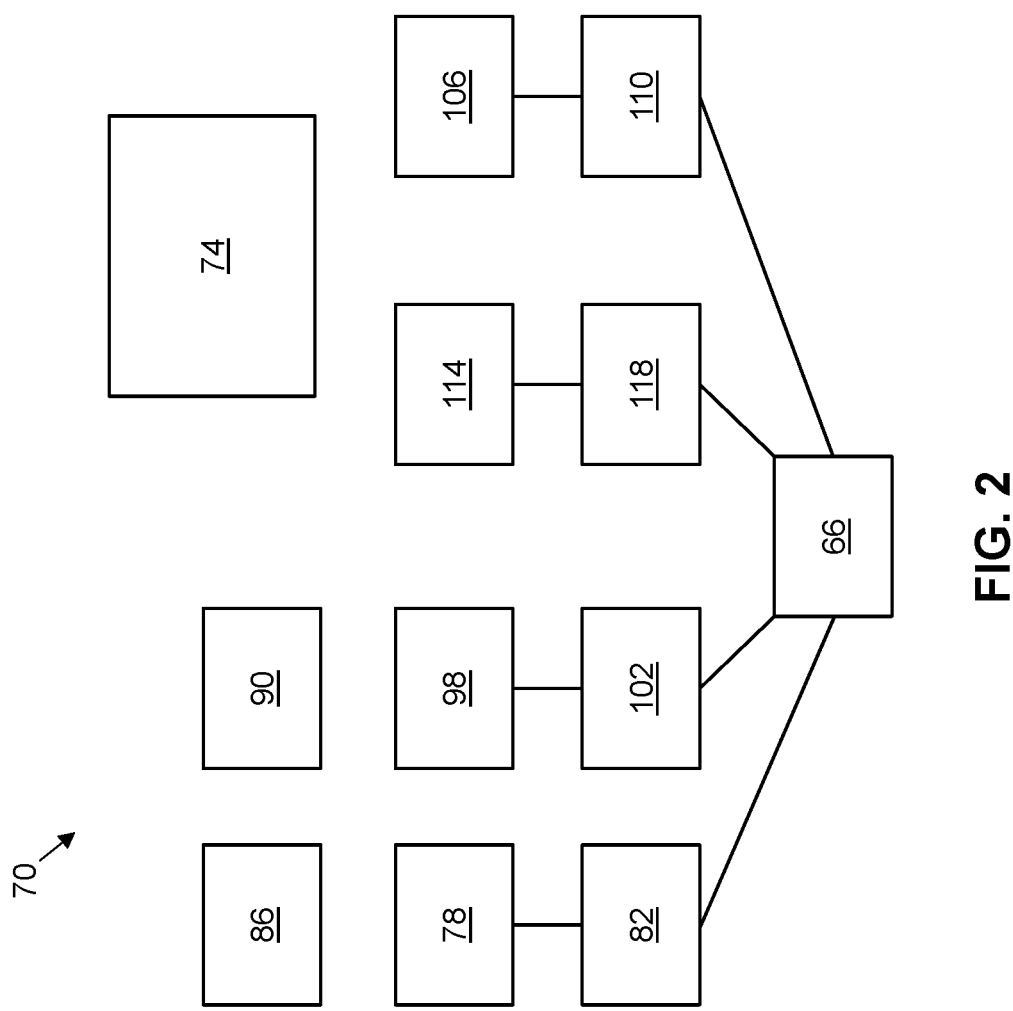
FIG. 2 is a schematic block diagram illustrating an application suitable for use with or in at least some of the present systems.

FIG. 2 illustrates an embodiment of an application 70 for aligning and/or superimposing (e.g., graphical) medical data with a perceived image of a patient (e.g., in real time). Application 70 can be coded in any suitable programming language, such as, for example, an object-oriented programming language (e.g., objective-C) and/or the like, to perform the functions described in this disclosure.

In the embodiment shown, application 70 includes one or more core data models (e.g., 74), one or more controllers (e.g., 78, 86, 90, 98, 106, 114), and one or more views (e.g., 82, 102, 110, 118) configured to perform the functions described in this disclosure. In some embodiments, such model(s), controller(s), and/or view(s) are merely conceptual (e.g., are not necessarily distinct physical pieces or segments of code, and may instead be combined into multiple combinations of model(s), controller(s), and/or view(s) to perform some or all of the functions described). In other embodiments, the model(s), controller(s), and/or view(s) described may be combined, omitted, and/or substituted in any combination to perform the functions described.

In the embodiment shown, application 70 broadly includes a core data model 74. Core data model 74 is configured to securely read and store (e.g., graphical) medical data. Core data model 74 can be configured to use database technology to store and manipulate the medical data. For example, core data model 74 may be configured to connect a healthcare professional to one or more patient files, each of which have one or more medical data files in the core data model. Core data model 74 can be configured to be secured to prevent unauthorized access to the medical data. For example, permission to access core data model 74 can be granted with proper authentication by a patient and/or a healthcare professional. In some embodiments, a patient has sole permission to access and share the patient's own medical data.

In this embodiment, application 70 can include a login controller 78 and a login view 82 to restrict access to a patient's medical data. Login controller 78 is configured to provide a patient's medical data upon presentation of a user's (e.g., the patient's and/or a healthcare professional's) valid credentials. Unless a user receives permission to view the medical data, the medical data cannot be viewed. Suitable user authentication can include password authentication and/or biometric authentication (e.g., facial recognition, finger prints, retinal scans, face recognition, voice prints, typing patterns, and/or the like). Login view 82 can be configured to display information (e.g., via display 66) at the direction of login controller 78. Application 70 can (e.g., also) include a user defaults controller 86. User defaults controller 86 can be configured to store persistent data (e.g., relating to view permissions and/or the like).

Medical data, as used herein, is referred to broadly and comprises medical data-based image(s), patient health records, healthcare provider records, medical procedure records, and/or the like. More particularly, medical data can comprise medical data-based image(s), such as, for example, image(s) depicting anatomical structure, neurological structure, hemodynamics, and/or the like, one or more of which can be graphically represented by at least one of the following: one or more computed axial tomography (CAT) images, magnetic resonance imaging (MRI) images, positron emission tomography (PET) images, ultrasound images, x-ray images, hemodynamic simulations, and/or the like. Such medical data-based image(s) can be formatted in a Digital Imaging and Communications in Medicine (DICOM) format, an image segmentation format, and/or the like. Further, such medical data-based image(s) may include spatial markers (e.g., identifiable by system 10) that correspond to locations of anatomical structures on a body of a patient (e.g., locations of one or both eye sockets, mouth, ears, anterior nasal aperture, and/or the like).

In this embodiment, application 70 includes a motion controller 90. Motion controller 90 can be configured to interface with one or more (e.g., underlying) sensors 94 of user interface device 14. One or more sensors 94 (e.g., which can interface with CPU 18 via I/O adapter 34 and system bus 22) can be configured to capture data indicative of one or more of the following attributes of user interface device 14: acceleration of the device (e.g., an accelerometer), angular velocity of the device (e.g., a gyroscope), a magnetic field detected by the device (e.g., a magnetometer), an atmospheric pressure surrounding the device (e.g., a barometer), and/or the like. Motion controller 90 can be configured to transmit data from one or more sensors 94 to one or more other controllers (e.g., 78, 86, 90, 98, 106, 114) of application 70 such that the controllers can perform functions described herein in response to the data captured by the sensors.

Application 70 includes a medical data controller 98 and a medical data view 102. Medical data view 102 can be configured to display information (e.g., on display 66) at the direction of medical data controller 98. Medical data controller 98 can be configured to run an application programming interface (API) for rendering on display 66 (e.g., via medical data view 102) two-dimensional (2D) and three-dimensional (3D) vector graphics using a platform, such as, for example, Open Graphics Library (OpenGL) (developed by Khronos Group in Beaverton, Oreg.), Metal (developed by Apple Inc. in Cupertino, Calif.), and/or the like. Medical data controller 98 can be configured to interface with one or more sensors 94 such that, when the sensors detect movement of user interface device 14 (e.g., movement caused by a user's handling of the user interface device relative to a body of a patient), the medical data controller 98 changes the orientation of the medical data shown in medical data view 102 in response to the movement. For example, medical data controller 98 can be configured to react to movement of user interface device 14 (e.g., in real-time) by rotating and/or panning the medical data-based image (e.g., to match the rotation and/or panning, respectively, of the user interface device) such that the medical data-based image appears to remain fixed relative to a perceived image of a patient during movement of the user interface device. Medical data controller 98 can be configured to interface with the medical data in a format such that the medical data controller provides efficient communication between the medical data controller and medical data view 102. For example, medical data controller 98, via medical data view 102, can be configured to display the medical data-based image on display 66 of user interface device 14 in DICOM format, image segmentation format, and/or the like. Medical data controller 98 can (e.g., also) be configured to react to user input (e.g., touches on touchscreen 54, keyboard 58, and/or mouse 62) in order to manipulate the medical data-based image (e.g., zoom, pan, rotate, and/or the like). For example, medical data view 102 can be configured to display controls on display 66, which can allow for manipulation of the medical data-based image (e.g., zooming, panning, rotating, and/or the like).

Application 70 includes an information controller 106 and an information view 110. Information controller 106 can be configured to obtain and/or format image metadata, such as, for example, technical metadata (e.g., spatial markers of an image, specifications about a medical device from which the medical data-based image was obtained, the date and/or time the medical data-based image was created and/or modified, and/or the like), descriptive metadata (e.g., keywords, captions, titles, comments and/or the like related to the medical data-based image), administrative metadata (e.g., usage and licensing rights, restrictions on reuse, contact information for the owner of the image, and/or the like), and/or the like. Information controller 106 can be configured to transmit image metadata to information view 110, which can display the image metadata on display 66.

Application 70 includes an image capture controller 114 and an image capture view 118. Image capture controller 114 is configured to obtain data indicative of a (e.g., real-time) perceived image captured by one or more (e.g., underlying) sensors 120 configured to capture an image (e.g., one or more cameras) of user interface device 14. Image capture controller 114 can (e.g., also) be configured to appropriately format image data obtained by sensor(s) 120 and transmit the image data to image capture view 118 (e.g., which can be configured to display information, for example, on display 66, at the direction of the image capture controller).

Image capture controller 114, via one or more sensors 120, can be configured to identify spatial markers on a patient's body. More particularly, for example, image capture controller 114 can be configured to interface with sensors 120 and/or a facial-recognition software in the underlying operating system of user interface device 14 to accomplish at least one of the following: (1) initiate registration of a spatial marker on a perceived image of a patient (e.g., wherein the spatial marker may correspond to an anatomical feature of the patient, such as, for example, one or both eye sockets, mouth, ears, anterior nasal aperture, and/or the like) with a corresponding (e.g., matching) spatial marker on a medical data-based image of the same patient (e.g., wherein the spatial marker may correspond to an anatomical feature of the patient, such as, for example, one or both eye sockets, mouth, ears, anterior nasal aperture, and/or the like), and (2) (e.g., continuously) update the position of the spatial marker(s) of the medical data-based image of the patient with the corresponding position of the spatial marker(s) of the perceived image of the patient as the user interface device is moved relative to the patient.

Image capture controller 114 can be configured to identify and/or update the position of the spatial marker(s) of the perceived image and/or the spatial marker(s) of the medical data-based image while the spatial marker(s) can be detected by sensors 120 (e.g., while the spatial marker(s) are within a field of view of the sensors). In this embodiment, by using a dead reckoning technique, image capture controller 114 can (e.g., also) be configured to update the position of the spatial marker(s) of the perceived image and/or the spatial marker(s) of the medical data-based image while the spatial marker(s) are undetectable by sensors 120 (e.g., while the spatial marker(s) are outside a field of view of the sensors).

As discussed in further detail below, display 66 of user interface device 14 can be configured to display any one or more of the present views (e.g., individually and/or simultaneously). For example, display 66 can be configured to simultaneously display (e.g., superimpose) the medical data-based image (e.g., via medical data view 102) with (e.g., real-time) the perceived image of a patient (e.g., via image capture view 118).

Figure 3:
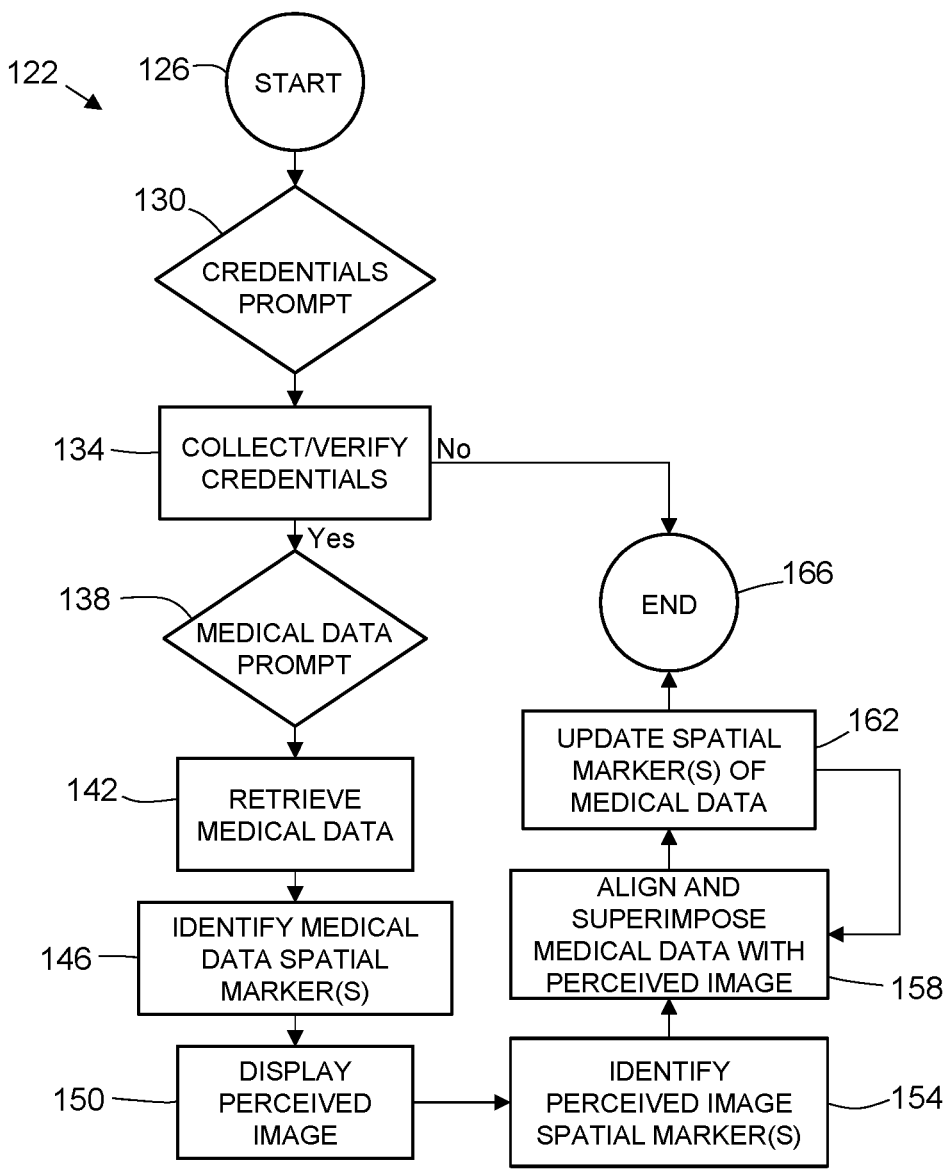
FIG. 3 is a flowchart of one embodiment of the present methods, including functions that can be included in embodiments of the present systems.

Referring now to FIG. 3, shown therein and designated by the reference numeral 122 is a flowchart illustrating an embodiment of the present methods, including functions that can be included (e.g., in various combinations) in embodiments of the present systems.

In the embodiment shown, the method begins at a starting block 126, and proceeds to a user credential prompt block 130, wherein a user is prompted to input credentials for accessing application 70, and thus, accessing a patient's medical data. Next, at block 134, the user's credentials may be collected and/or verified. In this embodiment, one of or both block 130 and block 134 may be carried out, at least in part, by user defaults controller 86, login controller 78, and/or login view 82. If the user does not provide proper credentials for accessing application 70, method 122 proceeds to block 166, wherein the method ends. However, if the user provides proper credentials for accessing application 70, method 122 proceeds to block 138, wherein the user is prompted to select the patient's medical data that will be viewed on display 66. Suitable types of medical data can be, for example, one or more of the types of medical data-based images described herein. At block 142, the medical data selected in block 138 is retrieved. For example, the medical data can be stored locally (e.g., on data storage device 50) and/or remotely (e.g., on a network in communication with communications adapter 38). In this embodiment, one of or both block 138 and block 142 may be carried out, at least in part, by core data model 74.

Next, at block 146, spatial markers in the medical data can be identified (e.g., by registering one or more spatial markers to the image metadata). In this embodiment, block 146 may be carried out, at least in part, by information controller 106, information view 110, medical data controller 98, medical data view 102, image capture controller 114, and/or image capture view 118. At block 150, user interface device 14 can be initialized to display a (e.g., real-time) perceived image of the patient on display 66 of the user interface device. At block 154, spatial markers in the (e.g., real-time) perceived image can be identified (e.g., using facial-recognition software in the underlying operating system of user interface device 14). In this embodiment, one of or both block 150 and block 154 may be carried out, at least in part, by image capture controller 114 and/or image capture view 118.

Next, at block 158, the medical data (e.g., medical data-based image) and the (e.g., real-time) perceived image of the patient can be viewed on display 66 simultaneously. For example, the spatial markers identified in the medical data can be aligned and superimposed with the spatial markers of the perceived image (e.g., in real time) such that the medical data is overlaid onto the perceived image of the patient. Thereafter, the spatial markers of the medical data may be (e.g., continuously) updated in block 162 such that the spatial markers of the medical data remain aligned and superimposed with the spatial markers of the perceived image (e.g., in real time). For example, the spatial markers of the medical data may appear to be fixed relative to the spatial markers of the perceived image such that, upon movement of user interface device 14 relative to the patient (e.g., movement that is detected by sensors 120, one or more of which interface with motion controller 90), the perceived image and the medical data remain aligned and superimposed relative to one another. In this embodiment, block 158 and block 162 may be repeated any number of times to continuously update the position of the spatial markers of the medical data relative to the position of the spatial markers of the perceived image. In this way and others, a patient's medical data-based image can be aligned and/or superimposed with the perceived image of the patient (e.g., in real time).

The above specification and examples provide a complete description of the structure and use of illustrative embodiments. Although certain embodiments have been described above with a certain degree of particularity, or with reference to one or more individual embodiments, those skilled in the art could make numerous alterations to the disclosed embodiments without departing from the scope of this invention. As such, the various illustrative embodiments of the methods and systems are not intended to be limited to the particular forms disclosed. Rather, they include all modifications and alternatives falling within the scope of the claims, and embodiments other than the one shown may include some or all of the features of the depicted embodiment. For example, elements may be omitted or combined as a unitary structure, and/or connections may be substituted. Further, where appropriate, aspects of any of the examples described above may be combined with aspects of any of the other examples described to form further examples having comparable or different properties and/or functions, and addressing the same or different problems. Similarly, it will be understood that the benefits and advantages described above may relate to one embodiment or may relate to several embodiments.

The claims are not intended to include, and should not be interpreted to include, means-plus- or step-plus-function limitations, unless such a limitation is explicitly recited in a given claim using the phrase(s) "means for" or "step for," respectively.

The invention claimed is:

1. A system comprising:
   a user interface device comprising:
      one or more sensors;
      a memory; and
      a processor coupled to the memory;
   wherein the processor is configured to:
      identify one or more spatial markers in a medical data-based image of a patient;
      in real-time:
         receive a real-time perceived image of the patient from the one or more sensors;
         based on a field of view of the one or more sensors, detect one or more spatial markers within the real-time perceived image, wherein the one or more spatial markers in the medical data-based image correspond to an anatomical feature of the patient and the one or more spatial markers in the real-time perceived image correspond to the anatomical feature of the patient;
         superimpose the medical data-based image of the patient with the real-time perceived image of the patient;
         align the one or more spatial markers in the superimposed medical data-based image with the respective one or more spatial markers in the real-time perceived image; and
         initiate display, via the user interface device, of the medical data-based image of the patient with the real-time perceived image such that the one or more spatial markers in the medical data-based image are aligned and superimposed with the one or more spatial markers in the real-time perceived image.

2. The system of claim 1, wherein the medical data-based image comprises at least one of the following: a computed axial tomography (CAT) image, a magnetic resonance imaging (MRI) image, a positron emission tomography (PET) image, an ultrasound image, and an x-ray image.

3. The system of claim 1, wherein the anatomical feature of the patient comprises one or more of the following: one or both eye sockets, a mouth, one or both ears, and an anterior nasal aperture.

4. The system of claim 1, wherein:
   the user interface further comprises a display screen;
   the processor is further configured to initiate display, the display screen, of the medical data-based image of the patient with the real-time perceived image such that the one or more spatial markers in the medical data-based image are aligned and superimposed with the one or more spatial markers in the real-time perceived image; and
   the real-time perceived image of the patient is captured by the one or more sensors.

5. The system of claim 1, wherein the one or more sensors are configured to detect movement of the position of the one or more spatial markers in the real-time perceived image; and wherein the processor is configured to update the position of the one or more spatial markers of the medical data-based image in response to the detected movement of the position of the one or more spatial markers in the real-time perceived image.

6. The system of claim 1, wherein the user interface device comprises a smartphone.

7. The system of claim 1, wherein the user interface device comprises wearable computer glasses.

8. The system of claim 1, wherein the user interface device comprises a tablet computer.

9. A computerized method comprising:
   identifying one or more spatial markers in a medical data-based image of a patient with a user interface device;
   in real-time:
      based on a field of view of the one or more sensors, detecting one or more spatial markers in a real-time perceived image of the patient with the user interface device, wherein the one or more spatial markers in the medical data-based image correspond to an anatomical feature of the patient and the one or more spatial markers in the real-time perceived image correspond to the anatomical feature of the patient;
      simultaneously displaying the medical data-based image of the patient and the real-time perceived image of the patient via the user interface device;
      aligning the one or more spatial markers in the medical data-based image with the one or more spatial markers in the real-time perceived image with the user interface device; and
      initiating display, via the user interface device, of the medical data-based image of the patient with the real-time perceived image such that the one or more spatial markers in the medical data-based image are aligned and superimposed with the one or more spatial markers in the real-time perceived image.

10. The method of claim 9, wherein the medical data-based image comprises at least one of the following: a computed axial tomography (CAT) image, a magnetic resonance imaging (MRI) image, a positron emission tomography (PET) image, an ultrasound image, and an x-ray image.

11. The method of claim 9, wherein the anatomical feature of the patient comprises one or more of the following: one or both eye sockets, a mouth, one or both ears, and an anterior nasal aperture.

12. The method of claim 9, wherein the real-time perceived image of the patient is captured by one or more sensors configured to capture an image.

13. The method of claim 9, comprising:
   detecting movement of the one or more spatial markers in the real-time perceived image; and
   updating on a display a position of the one or more spatial markers of the medical data-based image in response to the detected movement of the one or more spatial markers in the real-time perceived image.

14. The computerized method of claim 9, further comprising demonstrating in real-time the orientation, location, and/or spatial relevance of the anatomical feature of the patient relative to the perceived image with the user interface device.

15. The computerized method of claim 14, wherein the real-time perceived image of the patient is captured by the one or more sensors, and wherein the one or more sensors are included in a camera.

16. The computerized method of claim 14, wherein:
   the one or more sensors are configured to detect movement of the position of the one or more spatial markers in the real-time perceived image; and
   the processor is configured to update the position of the one or more spatial markers of the medical data-based image in response to the detected movement of the position of the one or more spatial markers in the real-time perceived image.

17. The system of claim 1, further comprising a login controller, wherein the login controller is configured to determine whether the medical data-based image of the patient matches the real-time perceived image of the patient.

18. The system of claim 17, wherein the login controller is configured to retrieve the medical data-based image of the patient based on a determination that the medical data-based image of the patient matches the real-time perceived image of the patient.

19. The system of claim 17, wherein the login controller is configured to restrict access to the medical data-based image based on a determination that the medical data-based image of the patient does not match the real-time perceived image of the patient.

* * * * *